(12) United States Patent
Hisada et al.

(10) Patent No.: US 8,043,852 B2
(45) Date of Patent: Oct. 25, 2011

(54) MONOCLONAL ANTIBODY SPECIFIC TO DENTIN-DERIVED HEPARAN SULFATE

(75) Inventors: Akiko Hisada, Kawagoe (JP); Ryosuke Takahashi, Kawagoe (JP); Hiroko Hanzawa, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 406 days.

(21) Appl. No.: 12/222,889

(22) Filed: Aug. 19, 2008

(65) Prior Publication Data

US 2009/0081809 A1 Mar. 26, 2009

(30) Foreign Application Priority Data

Sep. 25, 2007 (JP) ................................. 2007-247798

(51) Int. Cl.
- C12N 5/12 (2006.01)
- C12N 5/00 (2006.01)
- C07K 16/00 (2006.01)
- C07K 16/18 (2006.01)
- G01N 33/53 (2006.01)
- G01N 33/577 (2006.01)

(52) U.S. Cl. .................. 435/329; 530/388.1; 435/70.21; 435/326; 422/430

(58) Field of Classification Search ......................... None
See application file for complete search history.

(56) References Cited

U.S. PATENT DOCUMENTS 4,208,479 A * 6/1980 Zuk et al. .................... 435/7.9

FOREIGN PATENT DOCUMENTS

| JP | 63-052889 | 3/1988 |
| JP | 2007-078705 | 3/2007 |

OTHER PUBLICATIONS

Bai et al. "Differential expression of multiple cell-surface heparan sulfate proteoglycans during embryonic tooth development" J Histochem Cytochem. Aug. 1994;42(8):1043-54.*

De Angelis et al. "Syndecan-1 expression during postnatal tooth and oral mucosa development in rats aged from two days to six weeks" Aust Orthod J. Mar. 2002;18(1):1-6.*
Harlow, E. and Lane, D., Antibodies: A Laboratory Manual (1988) Cold Spring Harbor Laboratory Press, Cold Spring Harbor, NY, pp. 7, 59, 141-142, 148, 151, and 154-155.*
Takagi et al. "Immunohistochemical localization of glycosaminoglycans and proteoglycans in predentin and dentin of rat incisors" J Histochem Cytochem 1990 38: 319-324.*
Branford White, C.J. "Molecular organization of heparan sulphate proteoglycan from human dentine" Archives of Oral Biology vol. 23, Issue 12, 1978, pp. 1141-1144.*
Toin H. Van Kippevelt, Generation and Application of Type-Specific Anti-Heparan Sulfate Antibodies Using Phage Display Technology, The Journal of Biological Chemistry and Molecular Biology, Inc., May 22, 1998, pp. 12960-12966,vol. 273, No. 21.
Jacob Van Den Born, et al., Novel Heparan Sulfate Structures Revealed by Monoclonal Antibodies, The Journal of Biological Chemistry, Nat 27, 2005, vol. 280, No. 21.
Hayao Nakanishi, et al., Structural Differences Between Heparan Sulphates of Proteoglycan Involved in the Formation of Basement Membranes in Vivo by Lewis-lung-carcinoma-derived Cloned Cells with Different Metastatic Potentials, (1992) pp. 215-224.
Johan Ledin et al., Heparan Sulfate Structure in Mice With Genetically Modified Heparan Sulfate Production, The Journal of Biological Chemistry, Oct. 8, 2004, pp. 42732-42741, vol. 279, No. 41.
Nagai, K. et al. (Eds), "Sugar-Chain Science Building the Future", Kinpodo, 2005 pp. 112-113, 169-171, 198-199, 303-309, and 339-342.

* cited by examiner

*Primary Examiner* — N. C. Yang
*Assistant Examiner* — Christine Foster
(74) *Attorney, Agent, or Firm* — Antonelli, Terry, Stout & Kraus, LLP.

(57) ABSTRACT

The present invention provides a monoclonal antibody displaying excellent specificity against heparan sulfate saccharide chains for the analysis of heparan sulfate saccharide chains specific to dentin. The invention also provides a method of evaluating reproductive dentin using the monoclonal antibody. The anti-heparan sulfate monoclonal antibody reacts against dentin-derived heparan sulfate and in particular the anti-heparan sulfate monoclonal antibody reacts strongly and specifically with uncalcified predentin regions. In the method of evaluating dentin, the antibody is reacted against an isolated dentin-derived sample and the reaction is used in order to evaluate the development of dentin.

3 Claims, 7 Drawing Sheets
(5 of 7 Drawing Sheet(s) Filed in Color)

Fig. 4

- heparan sulfate (bovine kidney)
- heparin (derived from pig intestines)
- keratan sulfate (bovine cornea)
- keratan polysulfate (shark cartilage)
- dermatan sulfate (pig skin)
- chondroitin-4 *sulfate (whale* cartilage)
- chondroitin-6 *sulfate (shark* cartilage)
- chondroitin (from chondroitin *sulfate)*
- hyaluronic acid (hog skin)
- negative control (phosphate buffered saline)

immunofluorescent staining of developing porcine molar tissue section

A, C, E: developed dentin
B, D, F: regions less developed than A, C, E
-1: immunofluorescent staining image (green)
-2: Nomarski differential interference contrast image merged with epifluorescent image of nuclear staining (light blue) of identical section of 1 d: dentin
ob: odontoblasts
pd: predentin immunological staining of porcine tooth tissue section A: immunological staining image (brown) using C11C2
B: enlargement of dental pulp-predentin border of A
C: hematoxylin-eosin staining ab: alveolar bone
d: dentin
dp: dental pulp
ob: odontoblasts
pd: predentin

MONOCLONAL ANTIBODY SPECIFIC TO DENTIN-DERIVED HEPARAN SULFATE

CLAIM OF PRIORITY

The present application claims priority from Japanese Application JP 2007-247798 filed on Sep. 25, 2007, the content of which is hereby incorporated by reference into this application.

BACKGROUND OF THE INVENTION

1. Field of the Invention

The present invention relates to a novel monoclonal antibody binding specifically to dentin-derived heparan sulfate and to a method of evaluating dentin development (including regenerative dentin) using the monoclonal antibody.

2. Background Art

Heparan sulfate proteoglycan is present on cellular surfaces and in the extracellular matrix of animal cells and is known to play various roles in organic processes such as cellular differentiation, morphogenesis and cell adherence. Heparan sulfate proteoglycan consisted of core-protein and heparan sulfate chains. Heparan sulfate binds and modulates the activity of extracellular matrix and cell growth factors, and therefore implicates cellular proliferation, differentiation and adherence. Heparan sulfate exists in various structures resulting from modifications such as the sulfation or epimerization of a precursor having repeated disaccharide units of glucuronic acid and N-acetylglucosamine. It is assumed that oligosaccharide chains length is enough for physiological activity. The saccharide chain length and saccharide sequence, as well as the specific position of the sulfate group are important for cellular function. Heparan sulfate displays specific molecular structure related to cellular properties and interacts with specific molecules. Heparan sulfate is thought to be involved in the metastasis of cancer since abnormalities are observed in the saccharide chain structure during diseases such as cancer and heparan sulfate is important for cellular adherence. Furthermore it has been reported that grave abnormal phenotype arise in experimental animals as a result of genetic modification of heparan sulfate synthetase. (Nagai Yoshitaka (Editor) "Sugar-Chain Science Building the Future", Kinpodo (2005))

Heparan sulfate is an important constituent of humans and animals and is modified during stages of morphogenesis or disease. Consequently, analysis of heparan sulfate extracted and isolated from organisms is considered to be an extremely effective method of evaluating a developmental stage of tissue or for diagnosing cancer. In the context of regenerative therapies which are moving towards an application stage, it has been recently suggested that tissue evaluation techniques using heparan sulfate will be useful in evaluating regenerative tissue and moreover in controlling tissue morphogenesis.

Monoclonal antibodies which bind efficiently to heparan sulfate contained in a target tissue type are extremely useful for evaluating that tissue by analyzing the characteristics of heparan sulfate and evaluating the tissue through labeling, detecting or isolating heparan sulfate in the tissue.

Although an antibody against heparan sulfate proteoglycan which binds to core protein has been produced, few antibodies which bind specifically to the saccharide chain region have been produced. Up until the present, reports of an antibody binding to heparan sulfate chain regions have been in relation to an antibody recognizing heparan sulfate produced by isolating heparan sulfate proteoglycan antigen from cells or tissue rich in heparan sulfate (JP Patent Publication (Kokai) No. 63-52889A (1988) (JP Patent. No. 3006943) and JP Patent Publication (Kokai) No. 2007-78705A (2007)). Furthermore a plurality of single-chain antibodies of differing specificity have been screened using a phage display method with respect to heparan sulfate extracted from tissue. (Van Kuppevelt, T. H. et al., J Biol Chem 273(21): 12960-6. (1998)).

However immunization or antibody screening in particular require a large organic sample in order to obtain a corresponding amount of purified heparan sulfate proteoglycan or heparan sulfate. For example, the production of an antibody specific to dentin-derived heparan sulfate has encountered the difficulty of purifying heparan sulfate from tissue such as tooth predentin which does not allow for simple isolation.

As discussed above, the positions of the sulfate group and the sugar chains necessary for heparan sulfate activity highly differentiate (Nakanishi, H. et al., Biochem J 288: 215-224 (1992)) in response to the tissue type, its developmental stage (Ledin, J. et al., J Biol Chem 279(41): 42732-41 (2004) and van den Born, J. et al., J Biol Chem 280(21): 20516-23 (2005)) or in specific states (disease states). Consequently, an antibody specific to heparan sulfate derived from one type of tissue will not display the same reactivity to heparan sulfate derived from another tissue type. In other words, a monoclonal antibody displaying high sensitivity against a heparan sulfate species which is characteristic of a specific region or state (disease) will be a useful tool for distinguishing those tissues or states (diseases).

SUMMARY OF THE INVENTION

An object of the present invention is to provide a monoclonal antibody displaying excellent specificity against individual heparan sulfate sugar chains, which varies depending on tissue types for the purpose of analyzing tissue-specific heparan sulfate sugar chains. A further object of the present invention is to provide a method of evaluating regenerative dentin by using the monoclonal antibody specifically binding to developing dentin.

The present inventors have produced a hybridoma by fusion of a murine myeloma cell and a murine spleen cell which is immuno-sensitized in advance with an immunogenic tissue containing heparan sulfate proteoglycan, and have found that an anti-heparan sulfate monoclonal antibody of the subclass IgM produced by the hybridoma binds specifically to heparan sulfate in the immunogenic tissue. Consequently the production of an antibody binding to tissue-localized heparan sulfate was achieved without extracting or purifying heparan sulfate from the tissue.

In other words, the present invention relates to an anti-heparan sulfate monoclonal antibody wherein the antibody reacts strongly (specifically) with heparan sulfate derived from dentin and the intensity of the reaction increases depending on the development of the dentin.

The anti-heparan sulfate monoclonal antibody according to the present invention in particular reacts strongly with uncalcified predentin regions. The anti-heparan sulfate monoclonal antibody is specific to heparan sulfate chains and does not substantially react with heparin, keratan sulfate, keratan polysulfate, dermatan sulfate, chondroitin-4 sulfate, chondroitin-6 sulfate, or chondroitin.

The anti-heparan sulfate monoclonal antibody according to the present invention belongs to the immunoglobulin subclass IgM.

A preferred example of an anti-heparan sulfate monoclonal antibody according to the present invention is a monoclonal antibody produced by a hybridoma identified by Accession No. FERM BP-11009.

The present invention also provides a hybridoma identified by Accession No. FERM BP-11009 which produces an anti-heparan sulfate monoclonal antibody according to the present invention.

The present invention also provides a method of evaluating dentin development using an anti-heparan sulfate monoclonal antibody according to the present invention, the method comprising the steps of reacting a test sample derived from isolated dentin with an anti-heparan sulfate monoclonal antibody according to the present invention and evaluating a development of the dentin on the basis of the reaction.

The present invention also provides a kit for evaluating development of dentin comprising an anti-heparan sulfate monoclonal antibody according to the present invention.

The anti-heparan sulfate monoclonal antibody of the present invention reacts specifically with dentin-derived heparan sulfate and, moreover, the intensity of the reaction increases depending on development of the dentin. Thus it is possible to evaluate dentin development using an anti-heparan sulfate monoclonal antibody according to the present invention.

BRIEF DESCRIPTION OF THE DRAWINGS

The patent or application filed contains at least one drawing executed in color. Copies of this patent or patent application publication with color drawing(s) will be provided by the Office upon request and payment of the necessary fee.

FIG. 3 shows the reactivity in an ELISA assay when purified heparan sulfate is digested by heparitinase in Example 3. The vertical axis shows chromogenic development of the substrate reacting with alkali phosphatase used as a label in the ELISA assay by the absorbance at 405 nm. The horizontal axis shows the concentration of heparitinase.

FIG. 4 shows the reactivity against purified acidic mucopolysaccharides in a dot blotting assay in Example 3. Each acidic mucopolysaccharide was blotted on each dot and the dots of heparan sulfate stained brown are positive.

DETAILED DESCRIPTION OF THE PREFERRED EMBODIMENTS

Figure 1:
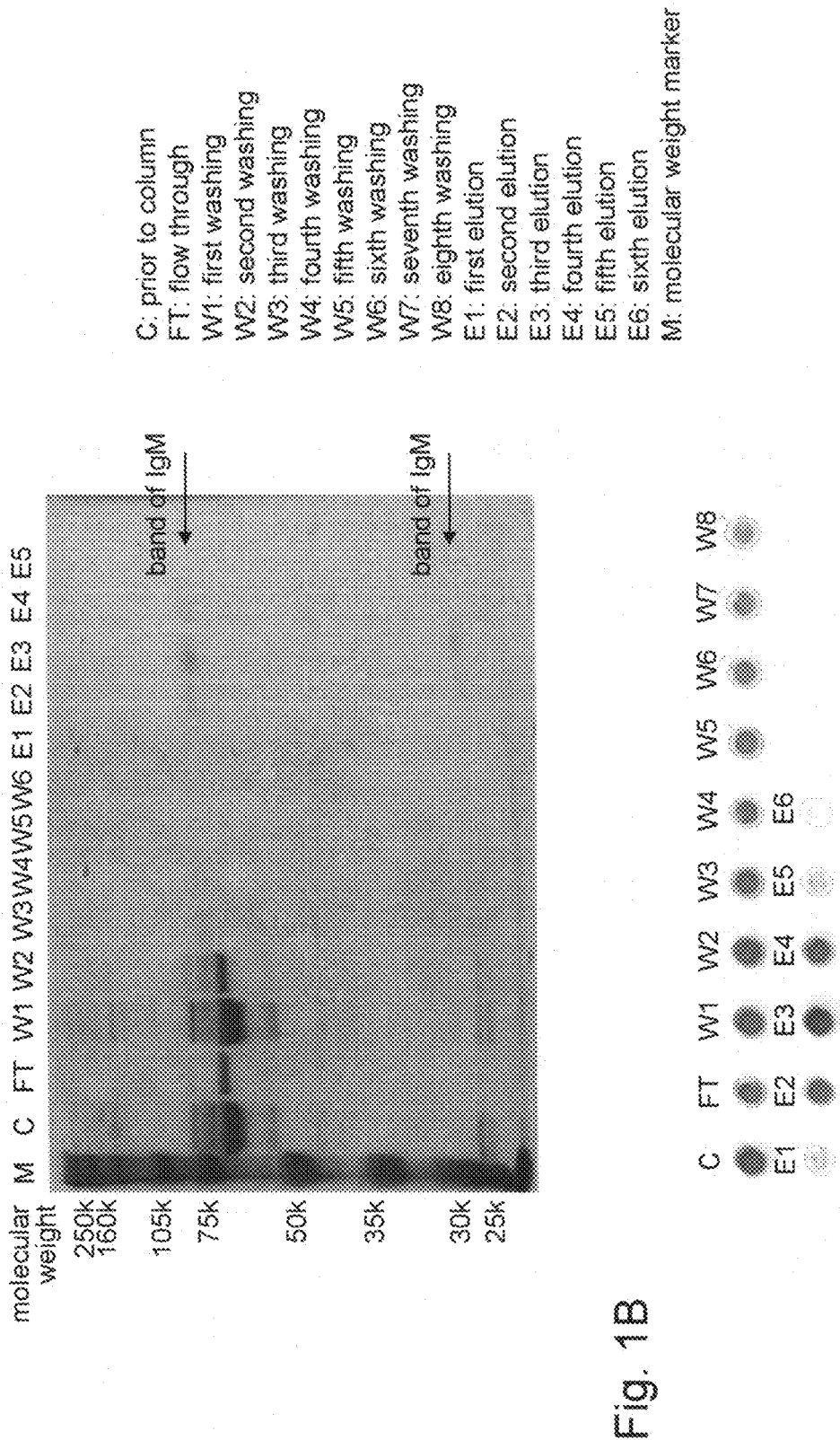
FIG. 1 shows the binding capacity of IgM to ImmunoAssist MG-PP column (Kanto Kagaku) by SDS-PAGE gel electrophoresis (FIG. 1A) and by a dot blotting assay using anti-mouse IgM μ-chain antibody (FIG. 1B) in purifying a C11C2 antibody in Example 2. In the result of SDS-PAGE gel electrophoresis, bands corresponding to IgM were stained blue using Gel Code® (PIERCE). In the result of dot blotting assay, a high concentration of IgM was detected in the dot fraction stained darkly blue. Based on the results of the two tests, it was determined to recover purified IgM from elutions 2, 3 and 4 (E2, E3, E4).

1. Anti-Heparan Sulfate Monoclonal Antibody According to the Present Invention

The anti-heparan sulfate monoclonal antibody of the present invention is a monoclonal antibody produced by a hybridoma formed by fusion of a murine myeloma cell with a murine spleen cell immunized with dentin tissue containing heparan sulfate. The monoclonal antibody reacts strongly with dentin-derived heparan sulfate chains.

The anti-heparan sulfate monoclonal antibody of the present invention does not react with core protein binding heparan sulfate but only binds to heparan sulfate chain regions. Furthermore the antibody of the present invention displays high specificity by reacting strongly only with heparan sulfate and not substantially reacting with other acidic mucopolysaccharides.

Furthermore the anti-heparan sulfate monoclonal antibody of the present invention reacts strongly with uncalcified predentin regions in tooth germ and the reaction strengthens in response to dentin development. Furthermore the border between dentin and dental pulp is clearly shown by the strong reaction with the predentin regions in the teeth. Therefore, as described hereafter, the anti-heparan sulfate monoclonal antibody of the present invention can be used to evaluate dentin development (including regenerative dentin).

2. Method of Producing Anti-Heparan Sulfate Monoclonal Antibody of the Present Invention The anti-heparan sulfate monoclonal antibody of the present invention requires the development of a novel hybridoma for its production. Hybridomas are produced by fusion of murine myeloma cells and murine spleen cells which are immunized with tissue containing heparan sulfate proteoglycan and selection of a hybridoma which produces monoclonal antibodies binding specifically to the target dentin-derived heparan sulfate.

The tissue containing immunogenic heparan sulfate proteoglycan may be selected from tooth-germ dentin, odontoblasts or the like [Bai, X. M. et al., J Histochem Cytochem 42(8): 1043-54. (1994)].

For example, organic tissue containing heparan sulfate is firstly fixed using a protein cross linking agent such as paraformaldehyde. When the sample contains hard tissue such as dentin, hard tissue is subjected to decalcification using 10% ethylenediamine tetraacetic acid (EDTA, pH 7.4) for example. Then the fixed and decalcified tissue is pulverized and administered together with an adjuvant to a mouse subcutaneously, intraperitoneally or intravenously. A BALB/c mouse may be used for immunization. The immunogen may be administered to the mouse several times at a two-week interval, and then immunization is completed by interperitoneal injection of antigen solution without adjuvant prior to cell fusion (for example, 3 days prior).

Murine spleen or lymph node is removed after the last immunization to obtain lymphocytes for use in cell fusion. SP2(Sp2/O—Ag14), NS1 (P3/NSI/1-Ag4-1) cells or the like may be used as the murine myeloma cells in the fusion process. Myeloma cells are mixed at a ratio of 10:1 for example with the lymphocytes. A polyethylene glycol method or the like may be used for cell fusion.

After the fusion operation, cells are inoculated to a 96-multiwell culture plate and hybridomas are cultured using a HAT medium for selection. After cell proliferation, supernatant is recovered from wells of the 96-multiwell culture plate in which a single colony has formed. Using supernatant respectively, hybridomas in a well displaying strong reactions to the tissue containing the target antigen substance are screened by immuno-histological staining method and by ELISA assay with the soluble tissue component containing the target antigen. The hybridomas are cloned using a limiting dilution method. Cloning is performed at least twice. For example, a HT medium is used during the first cloning process and a standard RPMI 1640 medium is used during the second cloning process. The 96-multiwell culture plate is inoculated with a suitable amount (for example, $1 \times 10^5$/well) of feeder spleen cells prepared from murine spleen during post cell-fusion culturing and cloning culturing. During the two cloning processes, hybridomas are selected from those which form single colonies in the well and furthermore which react strongly with the tissue containing the target antigen or a solubilized product thereof.

The hybridomas established by cloning are cultured in a growth medium. The antibody solution is obtained by recovering culture supernatant when cells reach subconfluence. Antibodies are obtained in the form of an ascites containing antibodies by inoculating a murine abdominal cavity with the established hybridoma. The resulting antibodies are purified in an affinity column for example to obtain purified IgM.

Heparan sulfate proteoglycan can be isolated from immunogenic tissue using an affinity column with a purified antibody that is established as a specific antibody binding to immunogenic tissue and identified as the antigen using amino acid analysis or mass spectrometric analysis.

Alternatively, it is possible to determine that the antigen is heparan sulfate proteoglycan by expression cloning techniques using mRNA extracted from immunogenic tissue. cDNA libraries prepared from the mRNA are expressed in cultured animal cells. Cells expressing the antigen are detected by immunostaining using the antibodies, and the gene is cloned and identified as the antigen gene.

Alternatively, it is possible to determine that the antigen is heparan sulfate or heparan sulfate proteoglycan by detecting the reaction to purified heparan sulfate or purified heparan sulfate proteoglycan by a dot blotting assay or an ELISA assay using established antibodies.

When heparan sulfate proteoglycan is identified as the relevant antigen, the fact that the antibody binds to the heparan sulfate chain rather than to the core protein can be determined by confirming via an ELISA assay or a dot blotting assay that immune reaction of the antibody is not deactivated after the antigen is treated with a protease.

By confirming via an ELISA assay or a dot blotting assay that the antibody immune reaction is lost after heparan sulfate or heparan sulfate proteoglycan is treated with heparitinase, the fact that antibody binds to the heparan sulfate chain rather than to the core protein can be determined.

3. Method of Evaluating Dentin Development (Including Regenerative Dentin)

The intensity of the reaction of the anti-heparan sulfate monoclonal antibody of the present invention against dentin increases depending on the developmental stage of the dentin in the sample. As a result, dentin development can be evaluated using the anti-heparan sulfate monoclonal antibody of the present invention. Dentin development is important, particularly for regenerative therapies in the area of dentistry.

More precisely, dentin development (regenerative dentin) can be evaluated using the reactivity of the anti-heparan sulfate monoclonal antibody of the present invention against a tissue section containing dentin. The reactivity of the antibody can be evaluated using known immunostaining methods (for example, fluorescent antibody techniques using a fluorescent dye, enzyme antibody techniques using enzymes such as peroxidase, methods using autoradiography antibodies binding radioactive isotopes, gold colloid methods or the like). The reaction may be a direct reaction applying antibodies directly to the sample or may be an indirect reaction utilizing secondary antibodies.

The evaluation may be performed by comparison with a suitable reference sample. However, when an empirical relationship between a developmental stage and a staining intensity is established, such relationship can be used in the evaluation.

4. Kit for Evaluation of Dentin Development (Including Regenerative Dentin)

A kit for evaluation of dentin (regenerative dentin) development according to the present invention contains anti-heparan sulfate monoclonal antibody as a necessary component.

The anti-heparan sulfate monoclonal antibody may be labeled with a suitable label (for example, an enzymatic label, radioactive label or fluorescent label) or may be suitably modified using biotin for example. The antibody may be immobilized on a suitable support or the support may be provided separately in the kit for immobilization of the antibody. The support may be a synthetic resin allowing for attachment of a protein, such as polyethylene, polypropylene, polybutylene, polystyrene, polymethacrylate, polyacrylamide or the like. The support may be glass, nitrocellulose, cellulose or an agarose support or a gel support. There is no particular limitation on the shape of the support, however the support may be provided as a microsphere, a particle such as a bead (for example, latex beads), a tube (inner wall) such as a micro-centrifuging tube or a micro titer plate (well).

In addition to the anti-heparan sulfate monoclonal antibody according to the present invention, a kit according to the present invention, may, as required, include other components required for performing the invention such as reagents for detecting labels, reaction buffers, enzymes, or substrates.

EXAMPLES

The invention will be described in detail hereafter with reference to the examples, however the invention is not thereby limited to the examples.

Example 1

Preparation of an Antibody-Producing Hybridoma Clone C11C2

(1) Preparation of Antigen

Impacted third molar tooth germ extracted from a porcine lower jaw was immersed in phosphate-buffered saline (PBS) containing 4% paraformaldehyde and fixed for 24 hours at room temperature while stirring. After washing with PBS, decalcification was performed by immersion in 10% ethylenediaminetetraacetic acid (EDTA) (pH 7.4) for one week. Dentin only was isolated from the decalcified tissue, which was converted to powdered form by freezing with liquid nitrogen and pulverizing. The resulting powder was suspended in 10% glycerol/PBS containing a protease inhibitor (Complete™, Boehringer Mannheim Ltd.). The suspension was processed by a homogenizer (mechanical crusher) on ice for 5 minutes and thereafter sonicated for a further 5 minutes on ice using a sonicator (ultrasonic crusher). The resulting suspension separated into two layers: a soluble fraction and an insoluble fraction. Immunosensitizing was performed using as an antigen a fraction capable of passing through a 26 G syringe needle used for subcutaneous injections.

(2) Preparation of Hybridoma

Antigen 20 µl (1 µg/µl) was mixed with an equivalent amount of complete adjuvant (Imject (registered trademark), Freund's Complete Adjuvant, PIERCE Co. Ltd). The mixture was subcutaneously injected to BALB/c mice (female, 5 weeks, Charles River Laboratories Japan Inc.) for sensitization. At the second immunosensitizing operation and thereafter, the same operation was repeated as described above at a two-week interval, except that complete adjuvant was replace with incomplete adjuvant (Imject (registered trademark), Freund's Incomplete Adjuvant, PIERCE Co. Ltd). Serum prepared from blood recovered from a murine caudal vein was serially diluted and used in an ELISA assay (described hereafter) to confirm a strong positive reaction to the antigen. Three days prior to cell fusion, final immunization was performed by interperitoneal injection of antigen solution (100 µg/200 µl/subject) not mixed with adjuvant. After three days, the murine spleen was removed, a dispersion of spleen cells was obtained, and NS1 cells derived from murine myeloma (P3/NSI/1-Ag4-1, Dainippon Sumitomo Pharma) were mixed with the spleen cells at a ratio of 1:10. Cell fusion was performed using polyethylene glycol (PEG, Roche) having a molecular weight of 1500. Firstly, the culture medium was completely removed by centrifuging the cell mixture for 5 minutes at 1000 rpm. Thereafter the spleen cells were fused with the myeloma cells by slow dropwise addition of PEG. The cells were resuspended by slow dropwise addition of HEPES medium [RPMI 1640 medium (Gibco Inc.), 10 mM HEPES (ICN Biomedicals Inc)] and centrifuged for 5 minutes at 1000 rpm to completely remove the HEPES medium containing PEG. A growth medium [RPMI 1640 medium, 10% FBS (CELLect (registered trademark) GOLD FBS, ICN Biomedicals Inc)] was added to the fused cells after fusion so that the spleen cells had a concentration of $2 \times 10^6$ cells/ml. An 8-channel multi-channel pipette was used to inoculate a 96-multiwell culture plate (MICROTEST™ Tissue Culture Plate, BD Falcon) with 100 µl lots of the resulting solution. The wells had been respectively pre-inoculated with $1 \times 10^5$ peritoneal feeder cells. The suspension of fused cells extracted from a single mouse was used to inoculate ten 96-multiwell culture plates. After one day, 100 µl lots of HAT medium [RPMI 1640 medium, 50×HAT solution (Dainippon Sumitomo Pharma), 10% FBS] was added to each well and selective culturing was carried out to develop only myeloma cells (hybridoma) fused with spleen cells.

(3) Screening of Hybridoma 14 days after cell fusion, inoculated wells of the 96-multiwell culture plate in which single colonies had formed were selected. The culture supernatant from each selected well was recovered and used in an ELISA assay (described hereafter) to select hybridoma producing antibodies displaying a positive reaction with the antigen. Using the culture supernatant of the selected hybridomas, an immunohistochemical staining with porcine tooth germ tissue sections (described hereafter) was used to identify wells wherein antibodies displaying a positive reaction were produced. Hybridomas from wells displaying positive reactions on two types of screening were cloned twice. The antibody screening during cloning processes was performed in the same manner as the screening after cell fusion.

(4) Screening by ELISA Assay

A sample for ELISA assay was prepared by treating enamel and dentin from tooth germ with a protein solubilizing agent (4M guanidine, 250 mM EDTA, protease inhibitor). The external solution dialyzed by the solubilized solution was recovered, concentrated and deionized for use as a non-collagen fraction. 100 µl lots of protein solution which is a non-collagen fraction (total protein concentration 100 µg/ml) were added to a 96 well ELISA plate (MaxiSorp™ Surface, Nunc) and allowed to stand overnight at 4° C. to solidify to the lower face of the plate. After blocking with Block Ace (Dainippon Sumitomo Pharma), 100 µl lots of hybridoma supernatant (or the immunized murine serum diluted 5000 times) as a primary antibody were added each well. After washing with washing buffer (0.05% Tween 20/PBS), 100 µl lots of anti-mouse IgG antibody labeled with alkali phosphatase (1/5000 dilution, Promega) were added as a secondary antibody to each well and incubated for one hour at 37° C. Thereafter washing was performed three times using washing buffer, a chromogenic substrate (pNPP ALKALINE PHOSPHATASE, CHEMICON) was added and absorbance was measured at 405 nm using a plate reader in order to select hybridomas producing antibodies with a high absorbance.

(5) Screening with an Immunohistochemical Staining Method Using Hybridoma Culturing Supernatant Third molar tooth germ excised from a porcine lower jaw were fixed in PBS containing 4% paraformaldehyde for one day at room temperature while stirring. After washing with PBS, decalcification was performed by immersion in 10% EDTA (pH 7.4) for 10 days at room temperature. After washing in water, decalcified molar tissue was dehydrated with ethanol dilution series, substituted from ethanol to xylene and then embedded in paraffin. Sections of 5 µm thickness were prepared with microtome. After de-paraffinizing the sections, blocking reagent (DAKO Protein Block, DAKO) was applied to sections for one hour at room temperature in order to inhibit non-specific binding of antibody to the tissue. The culture supernatant of the hybridoma for use as a primary antibody was fed dropwise and reacted overnight at 4° C. After washing in PBS containing 0.05% Tween 20, anti-mouse IgG antibody labeled with biotin (VECTASTAIN ABC Elite, Vector Laboratories) was applied for one hour and then washed with PBS containing 0.05% Tween 20. Methanol containing 0.3% $H_2O_2$ was applied for 30 minutes in order to deactivate endogenous peroxidase. After washing with PBS containing 0.05% Tween 20, an avidin-biotin complex labeled with Horseradish Peroxydase HRP (VECTASTAIN ABC Elite, Vector Laboratories) was applied for 30 minutes. After washing with PBS containing 0.05% Tween 20, diaminobenzidine (DAB chromogenic substrate, Vector Laboratories) was added and, after four minutes, the color development reaction was stopped by washing in deionized water. As a result, hybridomas producing an antibody displaying a strong color development reaction to dentin and odontoblast cells were selected.

(6) Cloning of Hybridoma

After the screening, selected hybridoma cells almost reaching confluence in wells of the multiwell plate were suspended using a Pasteur pipette and cellular fluid was drawn up to approximately 2 cm from the tip of the Pasteur pipette. In the primary cloning process, the cellular suspension was added in 20 ml of HT culture [RPMI1640 culture, 50×HT solution (Dainippon Sumitomo Pharma), 10% FBS]. In the secondary cloning process, the cellular suspension was added in 20 ml of growth medium. This cellular suspension was prepared as a four-concentration serial dilute solution up to a maximum 1000 dilution. 100 µl lots per well of the diluted suspension was added to a 96-multiwell culture plate, the wells of which had been respectively pre-inoculated with $1 \times 10^5$ spleen feeder cells. After culturing, wells in the 96-multiwell culture plate containing single colonies were selected, the culture supernatant was recovered and used in the screening process described above.

Hybridomas selected by this screening were named C11C2. The hybridoma clone C11C2 was deposited under Accession No. FERM P-21347 (transferred to Accession No. FERM BP-11009) with International Patent Organism Depositary (IPOD), National Institute of Advanced Industrial Science and Technology (AIST), Tsukuba Central 6, 1-1-1 Higashi, Tsukuba, Ibaraki, Japan on 21 Aug. 2007.

(7) Preparation of Culture Supernatant of C11C2 Hybridoma Clone and Cryopreservation of Hybridomas The C11C2 hybridoma clone producing monoclonal antibodies selected in the screening process after secondary cloning was cultured in growth medium using a cell culturing flask (175 cm$^2$). The culture supernatant and cells were collected when subconfluence was reached. The cells were suspended at a concentration of $2 \times 10^6$ cells/ml in a frozen-liquid Cell Banker (Nippon Zenyaku Kogyo Co., Ltd.) and cryopreserved in 1 ml lots. Antibody produced by the C11C2 hybridoma clone was secreted into the culture supernatant and hereafter monoclonal antibodies derived from the C11C2 hybridoma clone will be referred to as C11C2 antibody.

(8) Determination of Antibody Subclass

The C11C2 antibody subclass was identified as IgM by using a mouse monoclonal antibody typing kit (IgFast, BIO-CYTEX).

Example 2

Preparation of Purified C11C2 Antibody

300 µl/subject of 2,6,10,14-tetramethy pentadecane (common name: pristane) was injected into the peritoneum of a BALB/c mouse (female, 5 weeks old, Charles River Laboratories Japan Inc.) a week to ten days before inoculating with hybridoma. Hybridomas producing C11C2 antibody were cultured in a growth medium and cells were collected at the timing of subconfluence. The cells were suspended in HEPES medium at a concentration of $2 \times 10^6$ cells/ml and 500 µl/subject of the cell suspension was intraperitoneally injected into the murine which had been previously injected with pristane. About 1 to 2 weeks after injection, an ascites accumulating in the peritoneum was recovered.

The ascites was centrifuged for 10 minutes at 12000 rpm and the supernatant recovered so as to avoid sedimentation of the cells. 20 µl of supernatant was diluted with 3.5 ml of binding buffer [300 ml sodium chloride/10 mM PBS (pH 6.8)], filtered with a 0.45 µm syringe filter, loaded into a column which had been packed with 1 g of Immuno Assist MG-PP (Kanto Chemical Co., Inc.) and equilibrated with binding buffer. 2 ml of binding buffer was passed through the column 8 times in order to wash out non-bound protein. Then 1 ml of elution buffer [300 mM PBS (pH 6.8)] was passed though the column six times and recovered the second to the fourth elution buffer in order to obtain purified IgM. With regard to the fraction of purified IgM, each fractions from the column during outflow, elution and washing were recovered, monitored for purity using SDS-PAGE electrophoresis and compared for IgM content using a dot blot assay employing anti-IgM antibodies (ICN/CAPPEL Biomedicals, Inc.). The fraction obtained on the $2^{nd}$, $3^{rd}$ and $4^{th}$ elutions displayed a purified IgM band in the SDS-PAGE gel and was confirmed by dot blot assay to contain a large amount of IgM. The results are shown in FIG. 1.

In SDS-PAGE electrophoresis, 20 µl of the respective solutions were mixed with sample buffer (3% β-melcaptoethanol, 3% SDS, 10% glycerol, 0.3% bromphenol blue), subjected to thermal denaturation for 5 minutes at 95° C., loaded into 7.5% acrylamide gel and then electrophoresed. After electrophoresis, the gel was stained with Gel Code (PIERCE Co., Ltd).

In the dot blot assay, a PVDF membrane immersed in PBS was loaded onto a 96 well blotter, each well was inoculated using 10 µl of the respective solutions recovered from the column and was absorbed to the membrane for two hours. After residual solution was discharged, blocking was performed using Block Ace (Dainippon Sumitomo Pharma), anti-mouse IgM antibody labeled with alkali phosphatase (1/1000 dilution, ICN/CAPPEL Biomedicals, Inc.) was applied for 50 minutes and then washed using PBS containing 0.05% Tween 20. After the membrane was removed from the blotter and blocked using PBS containing 10% Block Ace for 30 minutes, a chromogenic reaction was induced for 10 minutes using Western Blue (Promega).

The fractions recovered from the $2^{nd}$, $3^{rd}$ and $4^{th}$ elutions were combined, loaded into a concentration column Centriplus YM-100 (MILLIPORE), and after centrifuging enrichment at 3000 g and 4° C., the buffer was replaced by PBS containing 10% glycerol and adjusted to a protein concentration of 1 mg/ml using PD-10 column (GE Healthcare).

Example 3

Testing of C11C2 Binding Specificity and C11C2 Binding Activity to Heparan Sulfate (1) ELISA-based Measurement of C11C2 Binding Activity to Heparan Sulfate Purified heparan sulfate (Seikagaku Corporation) was dissolved in 0.1 M sodium acetate buffer (pH 7.0), a dilution series prepared, and 100 µl lots used to inoculate a 96 well ELISA plate (MediSorp™ Surface, Nunc). When inoculating the 96 well ELISA plate with 100 µl lots, the dilution series of heparan sulfate was adjusted to 0, 0.5, 1, 2, 4, 6, 8, 10 µg per well. The plate inoculated with heparan sulfate solution was allowed to stand overnight at 4° C. and heparan sulfate was immobilize to the lower face of the plate. Blocking was performed using Block Ace (Dainippon Sumitomo Pharma).

Figure 2:
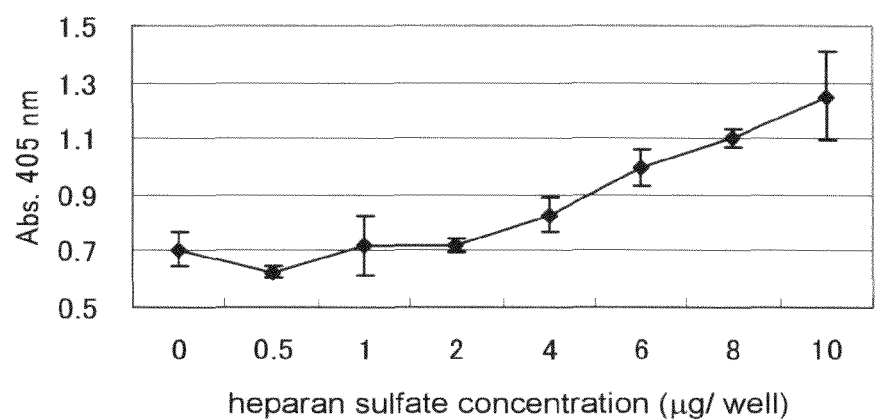
FIG. 2 shows the reactivity of C11C2 against purified heparan sulfate in the ELISA assay in Example 3. The vertical axis shows chromogenic development of the substrate reacting with alkali phosphatase used as a label in the ELISA assay by the absorbance at 405 nm. The horizontal axis shows the concentration of heparan sulfate.

Purified antibody solution (C11C2, 1 mg/ml) was diluted to 1/100 using PBS containing 10% Block Ace, added in 100 µl lots to each well and reacted for 2 hours. After washing with washing buffer (0.05%, Tween 20/PBS), a secondary antibody, anti-mouse IgM antibody labeled with alkali phosphatase (1/1000 dilution, ICN/CAPPEL Biomedicals, Inc.), was added in 100 µl lots to each well and reacted for 2 hours. Thereafter washing was performed three times using washing buffer, a 100 µl chromogenic substrate (pNPP ALKALINE PHOSPHATASE, CHEMICON) was added to each well and after reacting for three hours, absorbance was measured at 405 nm using a plate reader. In this manner, the binding activity of the C11C2 antibody to heparan sulfate was measured. The results are shown in FIG. 2. Since the absorbance increases when the concentration of heparan sulfate increases, C11C2 was shown to be an antibody which binds to heparan sulfate.

(2) Effect of Heparitinase Digestion of Purified Heparan Sulfate

Figure 3A:
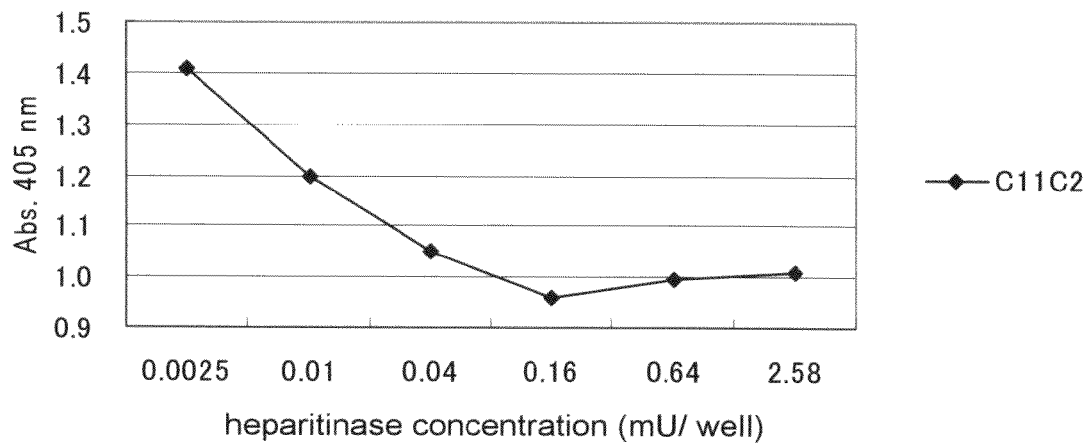
FIG. 3A shows the reactivity of the C11C2 antibody.
Figure 3B:
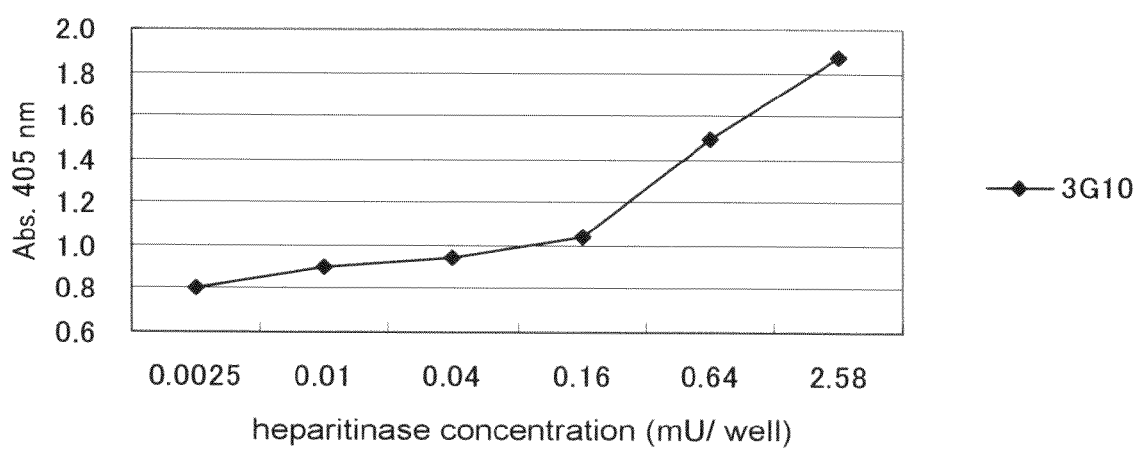
FIG. 3B shows the reactivity of a 3G10 antibody (Seikagaku Corporation) which reacts with epitopes produced when heparitinase is applied to heparan sulfate.

Purified heparan sulfate (Seikagaku Corporation) was dissolved in 0.1 M sodium acetate buffer (pH 7.0) to have a concentration of 0.1 µg/µl, and 100 µl lots were dispensed to a 96 well ELISA plate (MediSorp™ Surface, Nunc) thereby introducing 10 µg of heparan sulfate into each well. The plate was allowed to stand overnight at 4° C. so that heparan sulfate was immobilized to the lower face of the plate. 100 µl of 10 mM calcium acetate was added to each well and lightly pipetted. Heparitinase (Seikagaku Corporation) was diluted to the respective concentrations using 0.1 M sodium acetate buffer, added in 20 µl lots and allowed to react for two hours at 37° C. after gentle pipetting. The amount of heparitinase added to each well of the plate was adjusted to 0, 0.0025, 0.01, 0.04, 0.16, 0.645, 2.58 milliunits. After washing with washing buffer (0.05% Tween 20/PBS), blocking was performed using Block Ace (Dainippon Sumitomo Pharma). Purified antibody solution (1 mg/ml) was diluted to 1/100 using PBS containing 10% Block Ace, added in 100 µl lots to each well and reacted for 2 hours. Thereafter washing was performed using washing buffer, a secondary antibody, anti-mouse IgM antibody solution labeled with alkali phosphatase (1/1000 dilution, ICN/CAPPEL Biomedicals, Inc.), was added in 100 µl lots to each well and reacted for 2 hours. Washing was performed three times using washing buffer and 100 µl of a chromogenic substrate (pNPP ALKALINE PHOSPHATASE, CHEMICON) was added to each well. After reacting for 4 hours, absorbance was measured at 405 nm using a plate reader. Apart from C11C2 antibodies, an antibody 3G10 (Seikagaku Corporation) was used as a reference for recognizing new epitopes produced when heparan sulfate is digested by heparitinase. The results are shown in FIG. 3. The C11C2 antibody was shown to bind to heparan sulfate since it gradually stops reacting when the concentration of heparitinase increases and heparan sulfate is digested.

(3) Specificity of the C11C2 Antibody

In order to investigate the reactions of the C11C2 antibody with various types of acidic mucopolysaccharides, reactions with purified acidic mucopolysaccharides were compared using dot blot methods. Heparan sulfate, heparin, keratan sulfate, keratan polysulfate, dermatan sulfate, chondroitin-4 sulfate, chondroitin-6 sulfate, chondroitin, and hyaluronic acid (all Seikagaku Corporation) were dissolved in ultrapure water to a concentration of 2 µg/µl. A PVDF membrane immersed in PBS was loaded onto a 96 well blotter, each well was inoculated using 10 µl of various acidic mucopolysaccharide solutions. 10 µl of PBS was loaded as a negative control. The respective solutions were absorbed to the membrane for two hours. After residual solution was discharged, blocking was performed using Block Ace (Dainippon Sumitomo Pharma). Purified antibody solution (C11C2, 1 mg/ml) was diluted to 1/100 using PBS containing 10% Block Ace, added in 90 µl lots to each well and reacted for 2 hours. After washing in PBS containing 0.05% Tween 20, a secondary antibody, anti-mouse IgG antibody labeled with biotin (VECTASTAIN ABC Elite, Vector Laboratories), was reacted for 50 minutes and then washed with PBS containing 0.05% Tween 20. The mixture was reacted for 30 minutes with an avidin-biotin complex labeled with peroxydase (VECTASTAIN ABC Elite) and then washed with PBS containing 0.05% Tween 20. After the membrane was removed from the blotter and blocked for 30 minutes using PBS containing 10% Block Ace, a color development reaction was induced for 10 minutes using diaminobenzidine (DAB chromogenic substrate, Vector Laboratories). The results are shown in FIG. 4.

The results show that C11C2 antibodies did not react with chondroitin, chondroitin-6 sulfate, chondroitin-4 sulfate, dermatan sulfate, keratan sulfate, keratan polysulfate and heparin among the blotted various types of acidic mucopolysaccharides, reacted very weakly with hyaluronic acid and displayed a substantially clear positive reaction only with respect to the heparan sulfate dot. In other words, C11C2 antibodies were confirmed to react strongly and specifically with heparan sulfate.

Example 4

Figure 5:
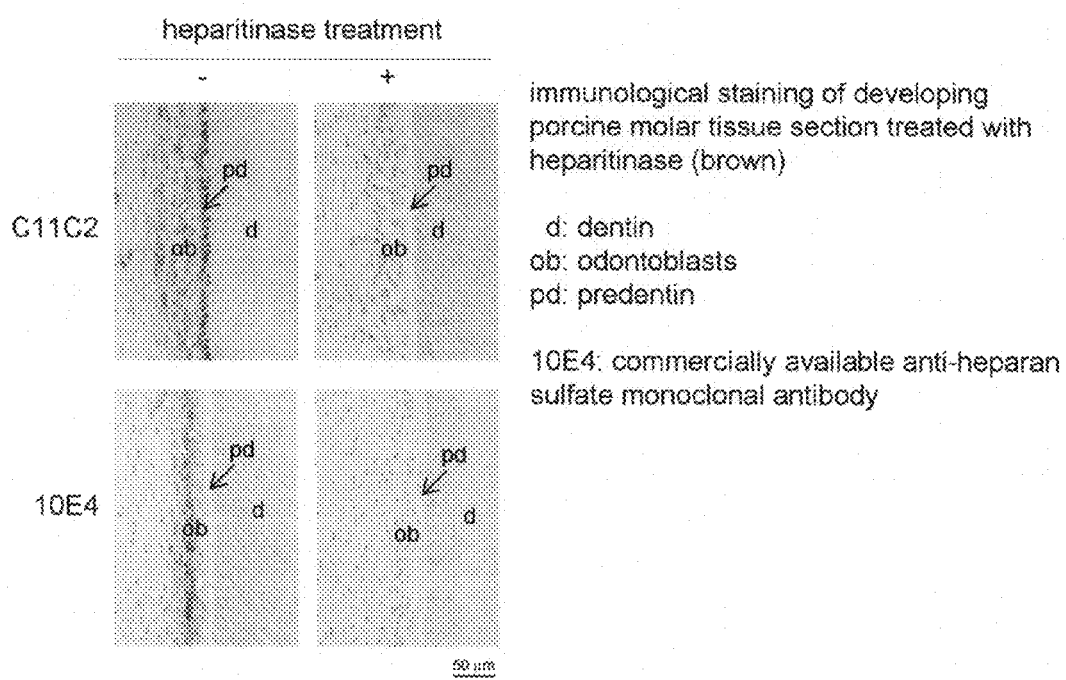
FIG. 5 shows a microscopic image showing the reactivity in immunological staining when a paraffin section of developing molar tissue containing dentin is treated with heparitinase in Example 4. (−) is an immunological stained image of the tissue section to which heparitinase has not been applied. (+) is an immunological stained image of the tissue section to which heparitinase has been applied. The upper half of the figure shows the reaction of the C11C2 antibody. The lower half of the figure shows the reaction of the commercially available anti-heparan sulfate antibody 10E4 (Seikagaku Corporation). The section stained brown shows a positive reaction of the immunological stain. The blue stain is developed color of the counter staining using hematoxylin. The immunological staining reaction to the tissue section was lost with respect to both the C11C2 and 10E4 antibodies as a result of treatment with heparitinase. Only C11C2 displayed a very strong reaction against predentin (pd) when heparitinase was not applied. No reaction was observed when heparitinase was applied.

Effect of Heparitinase Digestion of Heparan Sulfate Contained in Tooth Germ Tissue Paraffin sections of developing porcine molar tissue were prepared in the same manner as Example 1. After removing the paraffin, reactions were performed for two hours at 37° C. using a solution (50 mM sodium acetate buffer (pH 7.0), 5 mM calcium acetate) comprising heparitinase (Seikagaku Corporation) at a concentration of 0.005 milliunits/µl. After washing with PBS, treatment was performed for 30 minutes using a blocking agent (DAKO Protein Block, DAKO) in order to inhibit non-specific binding of antibody to the tissue. Purified antibody solution (1 mg/ml) was diluted to 1/100 in PBS, applied to the section and allowed to react overnight at 4° C. After washing in PBS containing 0.075% Brij35, a secondary antibody, anti-mouse IgG antibody labeled with biotin (VECTASTAIN ABC Elite, Vector Laboratories), was applied for 30 minutes and then washed with PBS containing 0.075% Brij35. Methanol containing 0.3% hydrogen peroxide was applied for 30 minutes in order to deactivate endogenous peroxidase. After washing with PBS containing 0.075% Brij35, an avidin-biotin complex labeled with peroxidase (VECTASTAIN ABC Elite, Vector Laboratories) was applied and reacted for 30 minutes. Washing was performed with PBS containing 0.075% Brij35, diaminobenzidine (DAB chromogenic substrate, Vector Laboratories) was added and reacted for two minutes. Thereafter washing with water was performed and counter staining was performed using hematoxylin. The results are shown in FIG. 5. Since reactions of C11C2 antibodies against the tissue section are lost as a result of digestion by heparitinase of heparan sulfate contained in the tissue, C11C2 antibodies binding to the tissue section clearly react specifically with heparan sulfate contained in the tissue.

Experiments carried out as described above using commercially available anti-heparan sulfate antibodies 10E4 (Seikagaku Corporation) did not demonstrate specific reactions against dentin including uncalcified predentin. Since staining in the periphery of odontoblasts disappeared as a result of heparitinase treatment, 10E4 was shown to react with heparan sulfate contained in tissue. However reaction of 10E4 with dentin was clearly shown to differ from C11C2.

Example 5

Evaluation of Dentin Development in Tooth Germ by Detection of Heparan Sulfate

Figure 6:
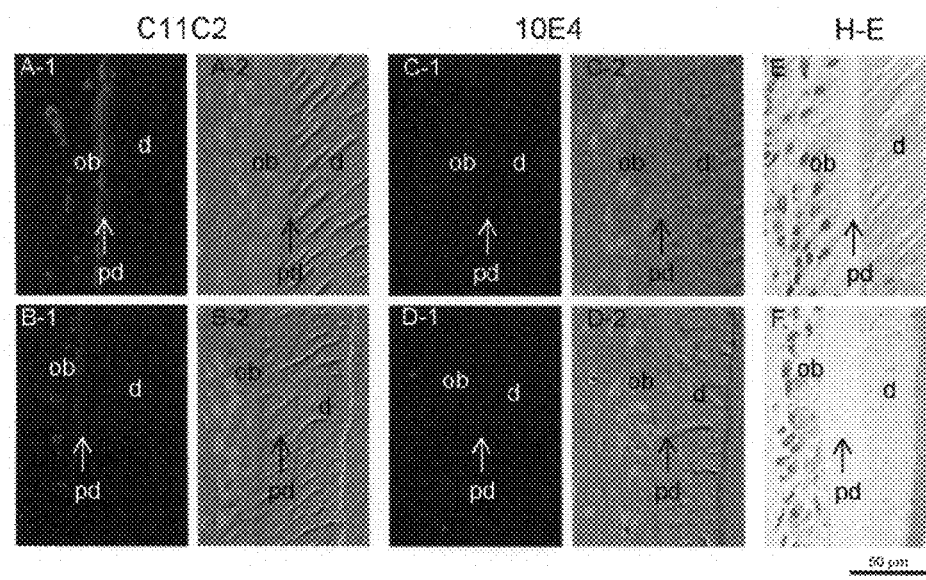
FIG. 6 shows a microscopic image of tissue sections containing odontoblasts and dentin at different developmental stages which have been subjected to immunofluorescence staining using C11C2 antibody or a commercially available anti-heparan sulfate antibody 10E4 (Seikagaku Corporation) in Example 5. The regions marked A-1 and B-1 developing a green color show a positive immunological staining reaction by C11C2.

Paraffin sections of porcine tooth germ were prepared in the same manner as Example 1. After removing the paraffin, an antigen retrieval treatment prior to immunostaining was performed by applying an enzymatic solution containing proteinase K (2546, Ambion) dissolved in PBS at a concentration of 100 µl/ml to a section on a slide glass and reacting for 10 minutes, then washing in PBS. Thereafter a blocking agent (DAKO Protein Block, DAKO) was applied for 10 minutes in order to inhibit non-specific binding of antibody to the tissue. Purified antibody solution was diluted to 1/100 in PBS, applied to the section, allowed to react overnight at 4° C. and then washed in PBS containing 0.075% Brij35 (Sigma-Aldrich). A secondary antibody, anti-mouse IgG antibody labeled with fluorescein isothiocyanate (FITC) (GE Healthcare BioSciences) diluted to 1/20, was applied for two hours and then washed with PBS containing 0.075% Brij35. Nuclear staining was effected with Bisbenzimide Hoechst 33258 (Wako Pure Chemicals) and embedded in the fluorescence encapsulating agent Perma Fluor (Thermo Shandon). The results of immunofluorescent staining by C11C2 antibodies of dentin at different developmental stages are shown in FIG. 6. C11C2 antibodies strongly react with predentin regions in which dentin has not calcified. In particular, a tendency was observed in which the intensity of the reaction increased depending on the progression of development.

Experiments carried out as described above using commercially available anti-heparan sulfate antibodies 10E4 (Seikagaku Corporation) did not demonstrate specific reactions with respect to dentin including uncalcified predentin. Furthermore no differences were evident in the intensity of staining depending on differences in developmental stages. In this manner, reaction of 10E4 with dentin were shown to differ from C11C2.

As discussed above, reactions of C11C2 antibodies against heparan sulfate display a strong sensitivity to dentin development in tooth germ and, as a result, it is expected that C11C2 antibodies may be useful in the evaluation of regenerative dentin or the like.

Example 6

Figure 7:
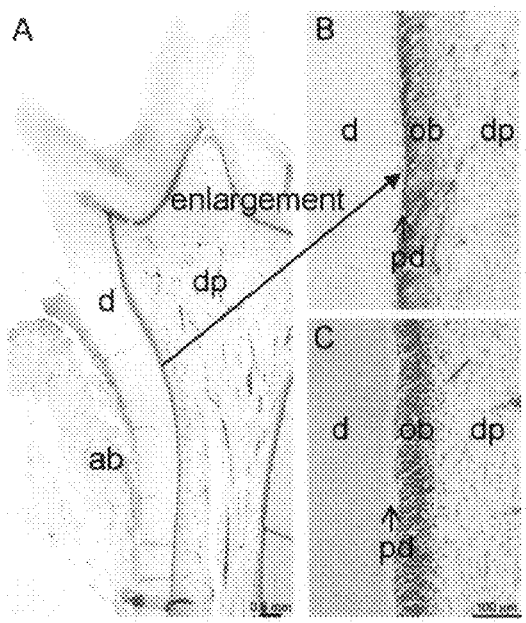
FIG. 7 shows a microscopic image of a developing molar tissue section which has been subjected to immunological staining using C11C2 in Example 6. The region stained brown shows a positive reaction of the immunological stain. The blue stain is developed color of the counter staining using hematoxylin. Strong immunostaining is observed along the pulp-dentin border.

Evaluation of the Dental Pulp-Dentin Border by Detection of Heparan Sulfate in Tooth Tissue Teeth excised from a porcine lower jaw were immersed in PBS containing 4% paraformaldehyde and fixed for three days at room temperature while stirring. After washing with PBS, decalcification was performed by immersion in a mixed solution of 10% sodium citrate and 22.5% formic acid at room temperature for 30 days. After washing in water, decalcified tooth was dehydrated with ethanol dilution series, substituted from ethanol to xylene and then embedded in paraffin. Sections of 5 µm thickness were prepared with microtome. After removing paraffin, a blocking agent (DAKO Protein Block, DAKO) was applied for 30 minutes in order to inhibit non-specific binding of antibody to the tissue. Purified antibody solution (C11C2, 1 mg/ml) was diluted to 1/100 using PBS, applied to the section and allowed to stand overnight at 4° C. After washing in PBS containing 0.075% Brij35, a secondary antibody, anti-mouse IgG antibody labeled with biotin (VECTASTAIN ABC Elite, Vector Laboratories), was applied for 30 minutes and then washed with PBS containing 0.075% Brij35. Methanol was applied for 30 minutes containing 0.3% hydrogen peroxide in order to deactivate endogenous peroxidase. After washing with PBS containing 0.075% Brij35, an avidin-biotin complex labeled with peroxydase (VECTASTAIN ABC Elite, Vector Laboratories) was applied and reacted for 30 minutes, then washed with PBS containing 0.075% Brij35. Diaminobenzidine (DAB chromogenic substrate, Vector Laboratories) was added and reacted for two minutes. Thereafter washing with water was performed and counter staining was performed using hematoxylin. The results are shown in FIG. 7. Since C11C2 reacts strongly with predentin and the dentin regions of odontoblasts in teeth, the dental pulp-predentin border is clearly shown and the outer shape of dental pulp is shown. In this manner, it is expected that C11C2 may be useful in evaluating reproductive regions of tooth in the context of reproductive therapies.

INDUSTRIAL APPLICABILITY

The anti-heparan sulfate monoclonal antibody of the present invention reacts specifically with dentin-derived heparan sulfate and, moreover, the reaction strengthens depending on dentin developments. Thus the present invention is useful in the area of dentistry for the evaluation of dentin development (reproductive dentin).

What is claimed is:

1. A purified anti-heparan sulfate monoclonal antibody produced by the hybridoma identified by Accession No. FERM BP-11009.

2. A hybridoma identified by Accession No. FERM BP-11009.

3. A kit for evaluating development of dentin comprising the antibody of claim 1.

* * * * *